United States Patent
Drolet et al.

(10) Patent No.: US 6,387,635 B1
(45) Date of Patent: May 14, 2002

(54) 2'-FLUOROPYRIMIDINE ANTI-CALF INTESTINAL PHOSPHATASE NUCLEIC ACID LIGANDS

(75) Inventors: Daniel Drolet; Larry Gold, both of Boulder, CO (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 09/941,964

(22) Filed: Aug. 28, 2001

Related U.S. Application Data

(62) Division of application No. 09/335,012, filed on Jun. 17, 1999, now Pat. No. 6,280,943.

(51) Int. Cl.[7] .................. C12Q 1/68; C12P 19/34; C07H 19/00; C07H 21/00; C07H 21/02
(52) U.S. Cl. .................. 435/6; 435/91.1; 435/91.2; 536/22.1; 536/23.1; 536/24.3
(58) Field of Search .................. 435/6, 91.1, 91.2; 536/22.1, 23.1, 24.3

(56) References Cited

U.S. PATENT DOCUMENTS

| | | | |
|---|---|---|---|
| 5,580,737 A | 12/1996 | Polisky | 435/6 |
| 5,723,323 A | 3/1998 | Kauffman et al. | 435/172.3 |
| 5,731,424 A | 3/1998 | Toothman | 536/23.1 |

FOREIGN PATENT DOCUMENTS

| | | |
|---|---|---|
| GB | 2 183 661 A | 6/1987 |
| WO | WO89/06694 | 7/1989 |
| WO | WO91/19813 | 12/1991 |
| WO | WO92/14843 | 9/1992 |

OTHER PUBLICATIONS

Ellington & Szostak (1990) Abstracts of papers presented at the 1990 meeting on RNA Processing, Cold Spring Harbor Laboratory, Cold Spring Harbor, NY, p. 84.
Joyce (1989) Gene 82:83–87.
Joyce & Inoue (1989) Nucleic Acids Research 17:711–722.
Kinzler & Vogelstein (1989) Nucleic Acids Research 17:3645–3653.
Kramer et al. (1974) J. Mol. Biol. 89:719–736.
Levisohn & Spiegelman (1969) Proc. Natl. Acad. Sci. USA 63:805–811.
Levisohn & Spiegelman (1968) Proc. Natl. Acad. Sci. USA 60:866–872.
Oliphant et al. (1989) Mol. Cell. Biol. 9:2944–2949.
Oliphant & Struhl (1988) Nucleic Acids Research 16:7673–7683.
Oliphant & Struhl (1987) Methods in Enzymology 155:568–583.
Oliphant et al. (1986) Gene 44:177–183.
Robertson & Joyce (1990) Nature 344:467–468.
Szostak, "Structure and Activity of Ribozymes," in Redesigning the Molecules of Life, (S.A. Benner ed.) Springer–Verlag Berlin Heidelberg, pp. 87–113, (1988).
Thiesen & Bach (1990) Nucleic Acids Research 18:3203–3208.

*Primary Examiner*—Jezia Riley
(74) *Attorney, Agent, or Firm*—Swanson & Bratschun, L.L.C.

(57) ABSTRACT

Methods are described for the identification and preparation of nucleic acid ligands to calf intestinal phosphatase. Included in the invention are specific RNA ligands to calf intestinal phosphatase identified by the SELEX method.

6 Claims, 5 Drawing Sheets

CIP NUCLEIC ACID LIGANDS: GROUP A

| ID | Sequence part 1 | Sequence part 2 | Sequence part 3 | SEQ ID NO: |
|---|---|---|---|---|
| DD172-2-2 | gggagacaagaauaaacgcucaa | acauaaaac aaaauaaccuuagccucggugcucuacgcaa | uucgacaggaggcucacaucaggc | 1 |
| DD172-2-17 | gggagacaagaauaa cgcucaa | acacaaaac aaaauaac uuggccucggugcucuacgcaa | uucgacaggaggcucacaacaggc | 2 |
| DD172-2-29 | gggagacaagaauaaacgcucaa | acacaaaacaaaauaaccuuagccucggugcucuacgcaa | uucgacaggaggcucacaacaggc | 3 |
| DD172-2-11.x | gggagacaaga aaacgcucaa | acacaaaac aaaauaaccuuagccucggugcucuacgcaa | uucgacaggaggcucacaacaggc | 4 |
| DD172-2-13.x | gggagacaagaauaaacgcucaa | acacaaaac aaaauaaccuuagccucggugcucuacgcaa | uucgacaggaggcucacaacaggcg | 5 |
| DD172-2-18.x | gggagacaagaauaaacgcucaa | acacaaaac aagauaaccuuagccucggugcucuacgcaa | uucgacaggaggcucacaacaggc | 6 |
| DD172-2-43 | gggagacaagaauaaacgcucaa | acacaaaac aaaa aaccuuagccucggugcucuacgcaa | uucgacaggaggaucacaacaggc | 7 |
| DD172-2-9 | gggagacaagaauaaacgcucaa | cacaaaac aaaauaaccuuagccucggugcucuacgcaa | uucgacaggaggcucacaacaggc | 8 |
| DD172-2-30 | gggagacaagaauaaacgcucaa | cacaaaac aaaauaaccuuagccucggugcucuacgcaa | uucgacaggaggcucacaacaggc | 9 |
| DD172-2-38.x | gggagacaagaauaaacgcucaa | cacaaaac aaaauaaccuuagccucggugcucuacgcaa | uucgacaggaagcucacaacaggc | 10 |
| DD172-2-14 | gggagacaagaauaaacgcucaa | acaaaac aaaauaacccuagccucggugcucuacgcaa | uucgacaggaggcucacaacaggc | 11 |
| DD172-2-37 | gggagacaagaauaaacgcucaa | acaaaaac aaaaauacuuagccucggugcucuacgcaa | uucgacaggaggcucacaacaggc | 12 |

CIP NUCLEIC ACID LIGANDS: GROUP B

| ID | Sequence part 1 | Sequence part 2 | Sequence part 3 | SEQ ID NO: |
|---|---|---|---|---|
| DD172-2-20 | gggagacaagaauaaacgcucaa | cgccaggcccuuaucagcgcggaacgcaugacccgucu | uucgacaggaggcucacaacaggc | 13 |
| DD172-2-23 | gggagacaagaauaaacgcucaa | cgccaggcccuuaucagcgcggaacgcaugacccgucu | uucgacaggaggcucacaacaggc | 14 |

Fig. 1

CIP NUCLEIC ACID LIGANDS: GROUP B (Continued)

| ID | Seq part 1 | Seq part 2 | Seq part 3 | # |
|---|---|---|---|---|
| DD172-2-25 | gggagacaagaauaaacgcucaa | cgccaggcccuuaucaagcgcggaacgcaugacccgucu | uucgacaggaggcucacaacaggc | 15 |
| DD172-2-31 | gggagacaagaauaaacgcucaa | cgccaggcccuuaucaagcgcggaacgcaugacccgucu | uucgacuggaggcucacaacaggc | 16 |
| DD172-2-39.x | gggagacaagaauaaacgcucaa | cgccaggcccuuaucaagcgcggaacgcaugacccgucu | uucgacaggaggcucacaacaggc | 17 |
| DD172-2-3 | nggagacaagaauaaacgcucaa | cgccaggcccuuaucaagcgcggaacgcaugacccgucu | uucgacaggaggcucacaacaggc | 18 |
| DD172-2-5 | gggagacaagaauaaacgcucaa | cgccaggcccuuaucaagcgcggaacgcaugacccgucu | uucgacaggaggcucacaacaggc | 19 |
| DD172-2-15.x | gggagacaagaauaaacgcucaa | cgccaggcccuuaucaagcgcggaacgcaugacccgucu | uucgacaggaggcucacaacaggc | 20 |
| DD172-2-26 | gggagacaagaauaaacgcucaa | cgccaggcccuuaucaagcgcggaacgcaugacccgucu | uucgacaggaggcucaucaacaggc | 21 |
| DD172-2-27.x | gggagacaagaauaaacgcucaa | cgccaggcccuuaucaagcgcggaacgcaugacccgucu | uucgacaggaggcucacaacaggc | 22 |
| DD172-2-28 | gagacaagaauaaacgcucaa | cgccaggcccuuaucaagcgcggaacgcaugacccgucu | uucgacaggaggcucacaacaggc | 23 |
| DD172-2-45.x | gggagacaagaauaaacgcucaa | cgccaggcccuuaucaagcgcggaacgcaugacccgucuu | ucgacaggaggcucacaacaggc | 24 |
| DD172-2-46 | gggagacaagaauaaacgcucaac | gccaggcccuuaucaagcgcggaacgcaugacccgucu | uucgacaggaggggcucacaacaggc | 25 |
| DD172-2-32 | gggagacaagaauaaacgcucaa | cgccaggcccuuaucaagcgcggaacgcaugacccgucu | uucgacaggaggcucacaacaggc | 26 |
| DD172-2-34 | gggagacaagaauuaaacgcucaa | cgccaggcccuuaucaagcgcggaacgcaugacccgucu | uucgacaggaggcucacaacaggc | 27 |
| DD172-2-40 | gggagacaagaaucaacgcucaa | cgccaggcccuuaucaagcgcggaacgcaugacccgucu | uucgacaggaggcucacaacaggc | 28 |

Fig. 1 (Continued)

CIP NUCLEIC ACID LIGANDS: GROUP B (Continued)

| | | | SEQ ID NO: |
|---|---|---|---|
| DD172-2-44 | gggagacaagaauaaacgcucaa | cgccaggcccuuaucaagcgcggaacgcaugacccgucu | uucgacaggaggcucacaacaggc | 29 |
| DD172-2-50 | gggagacaagaauaaacgcucaa | cgccaggcccuuaucaagcgcggaacgcaugacccgucu | uucgacaggaggcucacaacaggc | 30 |
| DD172-2-21 | gggagacaagaauaaacgcucaa | cgccaggcccuuaucaagcgcggaacgcaugacccgucu | ucgacaggaggcucacaacaggc | 31 |
| DD172-2-22.x | gggagacaagaauaaacgcucaa | cgccaggcccuuaucaagcgcggaacgcaugacccgucu | uucgacaggaggcucacaacaggc | 32 |
| DD172-2-41 | gggagacaagaauaaacgcucaa | cgccaggcccuuaucaagcgcggaacgcaugacccgucu | ucgacaggagcucacaacagc | 33 |
| DD172-2-19 | gggagacaagaauaaacgcucaa | cgccaggcccuuaucaagcgcggaacgcaugacccgucu | ucgacaggaggcucacaacagc | 34 |
| DD172-2-4 | gggagacaagaauaaacgcucaa | cgccaggcccuuaucaagcgcggaacgcaugacccgucu | uucgacaggaggcucacaacagc | 35 |
| DD172-2-1 | gggagacaagaauaaacgcucaa | cgccaggcccuuaucaagcgcguggaacgcaugacccgucu | uucgacaggaggcucacaacaggc | 36 |
| DD172-2-12 | gggagacaagaauaaacgcucaa | cgccaggcccuuaucaagcgcggaacgcacgacccgucu | uucgacaggaggcucacaacaggc | 37 |
| DD172-2-7 | gggagacaagaauaaacgcucaa | cgccaggcccuuaucaagcgcggaacgcaugacccguca | uucgacaggaggcucacaacaggc | 38 |
| DD172-2-36 | gggagacaagaauaaacgcucaa | ugccaggcccuuaucaagcgcggaacgcaugacccgucu | uucgacaggaggcucacaacaggc | 39 |
| | gggagacaagaauaaacgcucaa | gccaggcccuuaucaagcgcggaacgcaugacccgucu | uucgacaggaggcucacaacaggc | |

Fig. 1 (Continued)

CIP NUCLEIC ACID LIGANDS: GROUP C

```
DD172-2-24
gggagacaagaauaaacgcucaa  guaaaagcccucauagaacuaacaacgcgcucacgga  uucgacaggaggcucacaacaggc   40
DD172-2-6
gggagacaagaauaaacgcucaa  cgucauaaauguaaacaggauuauaagcgcgaccuaga                             41
DD172-2-16
                                                                uucgacaggaggcucacaacaggc
gggagacaagaauaaacgcucaa  gcgcaaagccuuucaagcucgugcuaucacugaa     uucgacaggaggcucacaacaggc   42
DD172-2-10
gggagacaagaauaaacgcucaa  cguccccccgucaagaucuccuccuccgcgucccuccc uucgacaggaggcucacaacaggc   43
[Clones DD172-2-1, DD172-2-5, DD172-2-13, DD172-2-18, dd-172-27, DD172-2-28, DD172-2-43, DD172-2-45,
DD172-2-46 had mistakes in the T7 promoter region.  Clone DD172-2-39 did not have readable
sequence in the T7 promoter region.]
```

TEMPLATES AND PRIMERS

```
40N8
gcctgttgtgagcctcctgtcgaa  nnnnnnnnnnnnnnnnnnnnnnnnnnnnnnnnnnnnnnnn  ttgagcgtttattcttgtctccc   44
5N8
taatacgactcactataggga gacaagaataaacgctcaa                                                    45
3N8
gcctgttgtgagcctcctgtcgaa                                                                     46
```

Fig. 1 (Continued)

2'-FLUOROPYRIMIDINE ANTI-CALF INTESTINAL PHOSPHATASE NUCLEIC ACID LIGANDS

RELATED APPLICATIONS

This application is a divisional of U.S. application Ser. No. 09/335,012, filed Jun. 17, 1999, entitled "2'-Fluoropyrimidine Anti-Calf Intestinal Phosphatase Nucleic Acid Ligands," now U.S. Pat. No. 6,280,943.

FIELD OF THE INVENTION

Described herein are high affinity nucleic acid ligands to calf intestinal phosphatase (CIP). Also described herein are methods for identifying and preparing high affinity nucleic acid ligands to CIP. The method used herein for identifying such nucleic acid ligands is called SELEX, an acronym for Systematic Evolution of Ligands by Exponential enrichment. Further disclosed are RNA ligands to CIP. Also included are oligonucleotides containing nucleotide derivatives chemically modified at the 2'-positions of pyrimidines. Additionally disclosed are RNA ligands to CIP containing 2'-F modifications. The invention also includes high affinity nucleic acid inhibitors of CIP. The oligonucleotides of the present invention are useful as diagnostic agents.

BACKGROUND OF THE INVENTION

Calf intestinal alkaline phosphatase (CIP) is a commonly used reporter enzyme for research and clinical assays. These assays typically use synthetic substrates that become detectable upon removal of phosphate groups by CIP. For example, one commonly used substrate is 1,2 dioxetane. This substrate becomes chemiluminescent upon the removal of phosphate groups by CIP. Another common substrate is the chromagen p-nitrophenylphosphate. Antibodies conjugated to CIP are widely used in ELISA, and nucleic acid probes linked to CIP can be used in a variety of nucleic acid detection schemes. Given the widespread use of CIP in various target detection schemes, it would be desirable to provide a class of ligands distinct from antibodies to which CIP could be conjugated.

The dogma for many years was that nucleic acids had primarily an informational role. Through a method known as Systematic Evolution of Ligands by EXponential enrichment, termed the SELEX process, it has become clear that nucleic acids have three dimensional structural diversity not unlike proteins. The SELEX process is a method for the in vitro evolution of nucleic acid molecules with highly specific binding to target molecules and is described in U.S. patent application Ser. No. 07/536,428, filed Jun. 11, 1990, entitled "Systematic Evolution of Ligands by EXponential Enrichment," now abandoned, U.S. Pat. No. 5,475,096 entitled "Nucleic Acid Ligands," and U.S. Pat. No. 5,270,163 (see also WO 91/19813), entitled "Methods for Identifying Nucleic Acid Ligands," each of which is specifically incorporated by reference herein in its entirety. Each of these applications, collectively referred to herein as the SELEX Patent Applications, describes a fundamentally novel method for making a nucleic acid ligand to any desired target molecule.

The SELEX process provides a class of products that are referred to as nucleic acid ligands or aptamers, each having a unique sequence, and which have the property of binding specifically to a desired target compound or molecule. Each SELEX-identified nucleic acid ligand is a specific ligand of a given target compound or molecule. The SELEX process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets in the SELEX method. The SELEX method applied to the application of high affinity binding involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule.

It has been recognized by the present inventors that the SELEX method demonstrates that nucleic acids as chemical compounds can form a wide array of shapes, sizes and configurations, and are capable of a far broader repertoire of binding and other functions than those displayed by nucleic acids in biological systems.

The basic SELEX method has been modified to achieve a number of specific objectives.

For example, U.S. patent application Ser. No. 07/960,093, filed Oct. 14, 1992, now abandoned, and U.S. Pat. No. 5,707,796, both entitled "Method for Selecting Nucleic Acids on the Basis of Structure," now abandoned (see, U.S. Pat. No. 5,707,796), describe the use of the SELEX process in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands," now abandoned, U.S. Pat. No. 5,763,177, entitled "Systematic Evolution of Nucleic Acid Ligands by Exponential Enrichment: Photoselection of Nucleic Acid Ligands and Solution SELEX" and U.S. Pat. No. 6,001,577, entitled "Systematic Evolution of Nucleic Acid Ligands by Exponential Enrichment: Photoselection of Nucleic Acid Ligands and Solution SELEX," describe a SELEX based method for selecting nucleic acid ligands containing photoreactive groups capable of binding and/or photocrosslinking to and/or photoinactivating a target molecule. U.S. Pat. No. 5,580,737, entitled "High-Affinity Nucleic Acid Ligands That Discriminate Between Theophylline and Caffeine," describes a method for identifying highly specific nucleic acid ligands able to discriminate between closely related molecules, which can be non-peptidic, termed Counter-SELEX. U.S. Pat. No. 5,567,588, entitled "Systematic Evolution of Ligands by EXponential Enrichment: Solution SELEX," describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX process-identified nucleic acid ligands containing modified nucleotides are described in U.S. Pat. No. 5,660,985, entitled "High Affinity Nucleic Acid Ligands Containing Modified Nucleotides," that describes oligonucleotides containing nucleotide derivatives chemically modified at the 5- and 2'-positions of pyrimidines. U.S. Pat. No. 5,580,737, supra, describes highly specific nucleic acid ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of Known & Novel 2' Modified Nucleosides by Intramolecular Nucleophilic Displacement," now abandoned, describes oligonucleotides containing various 2'-modified pyrimidines.

The SELEX method encompasses combining selected oligonucleotides with other selected oligonucleotides and non-oligonucleotide functional units as described in U.S. Pat. No. 5,637,459, entitled "Systematic Evolution of Ligands by EXponential Enrichment: Chimeric SELEX," and U.S. Pat. No. 5,683,867 entitled "Systematic Evolution of Ligands by EXponential Enrichment: Blended SELEX," respectively. These applications allow the combination of the broad array of shapes and other properties, and the efficient amplification and replication properties, of oligonucleotides with the desirable properties of other molecules.

The SELEX method further encompasses combining selected nucleic acid ligands with lipophilic compounds or non-immunogenic, high molecular weight compounds in a diagnostic or therapeutic complex as described in U.S. Pat. No. 6,011,020, entitled "Nucleic Acid Complexes." Each of the above described patents and applications which describe modifications of the basic SELEX procedure are specifically incorporated by reference herein in their entirety.

It is an object of the present invention to provide methods that can be used to identify nucleic acid ligands that bind with high specificity and affinity to calf intestinal phosphatase (CIP).

It is a further object of the present invention to obtain nucleic acid ligands to CIP that inhibit the activity of CIP when bound.

It is also an object of the present invention to obtain nucleic acid ligands to CIP that do not inhibit the phosphatase activity when bound to CIP.

An even further object of the invention is to provide a method for performing SELEX in a robotics-compatible microtiter plate format.

A still further object of the invention is to provide a method for absorbing SELEX targets to solid support surfaces, including microtiter plates, solely through hydrophobic interactions.

SUMMARY OF THE INVENTION

The present invention describes a method for isolating nucleic acid ligands that bind to calf intestinal phosphatase (CIP) with high specificity. The nucleic acid ligands of the invention can either be inhibitory or non-inhibitory. High affinity anti-CIP nucleic acid ligands can have many potential uses in assay systems that use CIP as a reporter enzyme.

The present invention also provides methods for immobilizing a SELEX target on a robotics-compatible microtiter plate solely through hydrophobic interactions. This method will allow high-throughput automation of the SELEX process.

BRIEF DESCRIPTION OF THE DRAWINGS

FIG. 1 illustrates nucleic acid ligand sequences obtained from the round 8 SELEX pool.

DETAILED DESCRIPTION OF THE PREFERRED EMBODIMENTS

Figure 2:
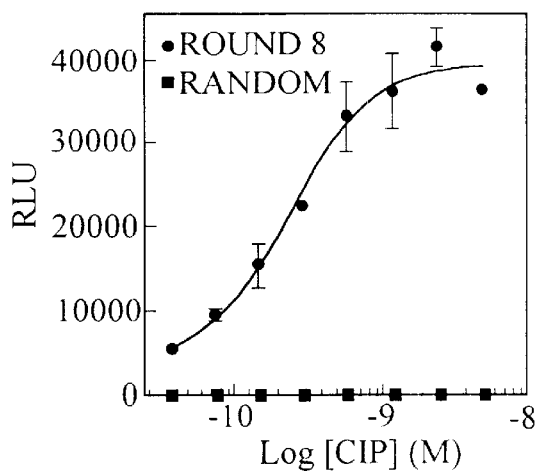
FIG. 2 illustrates CIP binding isotherms for the determination of the equilibrium dissociation constant at 37° C. for random 2'-F RNA (black squares) and the round 8 SELEX pool (black circles). Data are shown as the mean +/–the SEM (standard error margins) for duplicate determinations at each point.

The central method utilized herein for identifying nucleic acid ligands to CIP is called the SELEX process, an acronym for Systematic Evolution of Ligands by Exponential enrichment and involves: a) contacting the candidate mixture of nucleic acids with calf intestinal phosphatase, or expressed domains or peptides corresponding to calf intestinal phosphatase, b) partitioning between members of said candidate mixture on the basis of affinity to calf intestinal phosphatase, and c) amplifying the selected molecules to yield a mixture of nucleic acids enriched for nucleic acid sequences with a relatively higher affinity for binding to calf intestinal phosphatase.

Definitions

Various terms are used herein to refer to aspects of the present invention. To aid in the clarification of the description of the components of this invention, the following definitions are provided:

As used herein, "nucleic acid ligand" is a non-naturally occurring nucleic acid having a desirable action on a target. Nucleic acid ligands are often referred to as "aptamers". A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule. In the preferred embodiment, the action is specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. In the present invention, the target is calf intestinal phosphatase, or regions thereof. Nucleic acid ligands include nucleic acids that are identified from a candidate mixture of nucleic acids, said nucleic acid ligand being a ligand of a given target, by the method comprising: a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids.

As used herein, "candidate mixture" is a mixture of nucleic acids of differing sequence from which to select a desired ligand. The source of a candidate mixture can be from naturally-occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process.

As used herein, "nucleic acid" means either DNA, RNA, single-stranded or double-stranded, and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping.

"SELEX" methodology involves the combination of selection of nucleic acid ligands which interact with a target in a desirable manner, for example binding to a protein, with amplification of those selected nucleic acids. Optional iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. In the present invention, the SELEX methodology is employed to obtain nucleic acid ligands to calf intestinal phosphatase.

The SELEX methodology is described in the SELEX Patent Applications.

"SELEX target" or "target" means any compound or molecule of interest for which a ligand is desired. A target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation. In this application, the SELEX target is calf intestinal phosphatase. In particular, the SELEX targets in this application include purified calf intestinal phosphatase, and fragments thereof, and short peptides or expressed protein domains comprising calf intestinal phosphatase.

As used herein, "solid support" is defined as any surface to which molecules may be attached through either covalent or non-covalent bonds. This includes, but is not limited to, membranes, microtiter plates, magnetic beads, charged paper, nylon, Langmuir-Bodgett films, functionalized glass, germanium, silicon, PTFE, polystyrene, gallium arsenide, gold, and silver. Any other material known in the art that is capable of having functional groups such as amino, carboxyl, thiol or hydroxyl incorporated on its surface, is also contemplated. This includes surfaces with any topology, including, but not limited to, spherical surfaces and grooved surfaces.

Preparation of Nucleic Acid Ligands to Calf Intestinal Phosphatase

In the preferred embodiment, the nucleic acid ligands of the present invention are derived from the SELEX methodology. The SELEX process is described in U.S. patent application Ser. No. 07/536,428, entitled "Systematic Evolution of Ligands by Exponential Enrichment," now abandoned, U.S. Pat. No. 5,475,096, entitled "Nucleic Acid Ligands," and U.S. Pat. No. 5,270,163 (see also WO 91/19813), entitled "Methods for Identifying Nucleic Acid Ligands." These applications, each specifically incorporated herein by reference, are collectively called the SELEX Patent Applications.

The SELEX process provides a class of products which are nucleic acid molecules, each having a unique sequence, and each of which has the property of binding specifically to a desired target compound or molecule. Target molecules are preferably proteins, but can also include among others carbohydrates, peptidoglycans and a variety of small molecules. SELEX methodology can also be used to target biological structures, such as cell surfaces or viruses, through specific interaction with a molecule that is an integral part of that biological structure.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: a) to assist in the amplification steps described below, b) to mimic a sequence known to bind to the target, or c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity for the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The basic SELEX method has been modified to achieve a number of specific objectives. For example, U.S. patent application Ser. No. 07/960,093, filed Oct. 14, 1992, now abandoned, and U.S. Pat. No. 5,707,796, both entitled "Method for Selecting Nucleic Acids on the Basis of Structure," now abandoned (see, U.S. Pat. No. 5,707,796), describe the use of the SELEX process in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands," now abandoned, U.S. Pat. No. 5,763,177, entitled "Systematic Evolution of Nucleic Acid Ligands by Exponential Enrichment: Photoselection of Nucleic Acid Ligands and Solution SELEX" and U.S. Pat. No. 6,001,577, entitled "Systematic Evolution of Nucleic Acid Ligands by Exponential Enrichment: Photoselection of Nucleic Acid Ligands and Solution SELEX," all describe a SELEX based method for selecting nucleic acid ligands containing photoreactive groups capable of binding and/or photocrosslinking to and/or photoinactivating a target molecule. U.S. Pat. No. 5,580,737, entitled "High-Affinity Nucleic Acid Ligands That Discriminate Between Theophylline and Caffeine," describes a method for identifying highly specific nucleic acid ligands able to discriminate between closely related molecules, termed Counter-SELEX. U.S. Pat. No. 5,567,588, entitled "Systematic Evolution of Ligands by Exponential Enrichment: Solution SELEX," describes a SELEX-based method which achieves highly efficient partitioning between oligonucleotides having high and low affinity for a target molecule. U.S. Pat. No. 5,496,938, entitled "Nucleic Acid Ligands to HIV-RT and HIV-1 Rev," describes methods for obtaining improved nucleic acid ligands after SELEX has been performed. U.S. Pat. No. 5,705,337, entitled "Systematic Evolution of Ligands by Exponential Enrichment: Chemi-SELEX," describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. Pat.2 No. 5,660,985, entitled "High Affinity Nucleic Acid Ligands Containing Modified Nucleotides," that describes oligonucleotides containing nucleotide derivatives chemically modified at the 5- and 2'-positions of pyrimidines. U.S. Pat. No. 5,637,459, supra, describes highly specific nucleic acid ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement," now abandoned, describes oligonucleotides containing various 2'-modified pyrimidines.

The SELEX method encompasses combining selected oligonucleotides with other selected oligonucleotides and non-oligonucleotide functional units as described in U.S. Pat. No. 5,637,459, entitled "Systematic Evolution of Ligands by Exponential Enrichment: Chimeric SELEX" and U.S. Pat. No. 5,683,867, entitled "Systematic Evolution of Ligands by Exponential Enrichment: Blended SELEX," respectively. These applications allow the combination of the broad array of shapes and other properties, and the efficient amplification and replication properties, of oligonucleotides with the desirable properties of other molecules.

In U.S. Pat. No. 5,496,938 methods are described for obtaining improved nucleic acid ligands after the SELEX process has been performed. This patent, entitled "Nucleic Acid Ligands to HIV-RT and HIV-1 Rev," is specifically incorporated herein by reference.

One potential problem encountered in the diagnostic use of nucleic acids is that oligonucleotides in their phosphodiester form may be quickly degraded in body fluids by intracellular and extracellular enzymes such as endonucleases and exonucleases before the desired effect is manifest. Certain chemical modifications of the nucleic acid ligand can be made to increase the in vivo stability of the nucleic acid ligand or to enhance or to mediate the delivery of the nucleic acid ligand. See, e.g., U.S. patent application Ser. No. 08/117,991, filed Sep. 8, 1993, now abandoned, and U.S. Pat. No. 5,660,985, both entitled "High Affinity Nucleic Acid Ligands Containing Modified Nucleotides," which are specifically incorporated herein by reference. Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping. In preferred embodiments of the instant invention, the nucleic acid ligands are RNA molecules that are 2'-fluoro (2'-F) modified on the sugar moiety of pyrimidine residues.

The modifications can be pre- or post-SELEX process modifications. Pre-SELEX process modifications yield nucleic acid ligands with both specificity for their SELEX target and improved in vivo stability. Post-SELEX process modifications made to 2'-OH nucleic acid ligands can result in improved in vivo stability without adversely affecting the binding capacity of the nucleic acid ligand.

Other modifications are known to one of ordinary skill in the art. Such modifications may be made post-SELEX process (modification of previously identified unmodified ligands) or by incorporation into the SELEX process.

The nucleic acid ligands of the invention are prepared through the SELEX methodology that is outlined above and thoroughly enabled in the SELEX applications incorporated herein by reference in their entirety. The SELEX process can be performed using purified calf intestinal phosphatase, or fragments thereof as a target. Alternatively, full-length calf intestinal phosphatase, or discrete domains of calf intestinal phosphatase, can be produced in a suitable expression system. Alternatively, the SELEX process can be performed using as a target a synthetic peptide that includes sequences found in calf intestinal phosphatase. Determination of the precise number of amino acids needed for the optimal nucleic acid ligand is routine experimentation for skilled artisans.

In some embodiments, the nucleic acid ligands become covalently attached to their targets upon irradiation of the nucleic acid ligand with light having a selected wavelength. Methods for obtaining such nucleic acid ligands are detailed in U.S. patent application Ser. No. 08/123,935, filed Sep. 17, 1993, entitled "Photoselection of Nucleic Acid Ligands," now abandoned, U.S. Pat. No. 5,763,177, entitled "Systematic Evolution of Nucleic Acid Ligands by Exponential Enrichment: Photoselection of Nucleic Acid Ligands and Solution SELEX" and U.S. Pat. No. 6,001,577, entitled "Systematic Evolution of Nucleic Acid Ligands by Exponential Enrichment: Photoselection of Nucleic Acid Ligands and Solution SELEX," each of which is specifically incorporated herein by reference in its entirety.

In preferred embodiments, the SELEX process is carried out using full length calf intestinal phosphatase coated on the surface of wells of a plastic microtiter plate. A candidate mixture of single stranded RNA molecules is then contacted with the bound calf intestinal phosphatase in the wells of the plate. After incubation for a predetermined time at a selected temperature, the wells of the plate are washed to remove unbound candidate nucleic acid ligand. The nucleic acid ligand that binds to the calf intestinal phosphatase is then released into solution, and amplified using the Polymerase Chain Reaction. The amplified candidate mixture is then used to begin the next round of the SELEX process.

After nucleic acid ligands with the desired affinity for calf intestinal phosphatase are isolated, they can be assayed to determine if they inhibit the activity of the enzyme. This can be performed using any of the numerous methods known in the art for the determination of calf intestinal phosphatase activity. For example, in some embodiments, the assay used can be the chromagenic p-Nitrophenylphosphate assay.

The nucleic acid ligands isolated by the method of the instant invention have a great number of applications in assays systems that use calf intestinal phosphatase. For example, in some embodiments, a non-inhibitory nucleic acid ligand is conjugated to calf intestinal phosphatase in such a way that the calf intestinal phosphatase does not bind to the affinity site on the nucleic acid ligand. The calf intestinal phosphatase molecule to which the nucleic acid ligand is conjugated can itself be conjugated to a target analyte specific reagent. When this analyte specific reagent binds to its target analyte, calf intestinal phosphatase can be added to the solution, and will bind to the nucleic acid ligand conjugated to the original molecule of calf intestinal phosphatase. This binding of additional calf intestinal phosphatase to the target analyte specific reagent will result in a greatly enhanced signal upon addition of the detectable substrate. In this way, the sensitivity of many assay systems that use analyte specific reagents conjugated to calf intestinal phosphatase—such as calf intestinal phosphatase conjugated antibodies—can be dramatically increased.

In other embodiments, a nucleic acid molecule can be synthesized in which the calf intestinal phosphatase nucleic acid ligand sequence is contiguous with a nucleic acid ligand sequence directed against another target molecule. The resulting nucleic acid ligand can bind to the target molecule, and this binding can then be detected by adding calf intestinal phosphatase and the appropriate substrate. In this way, the amount of target analyte present is directly proportional to the amount of signal generated by CIP activity on the substrate.

In other embodiments, non-inhibitory CIP nucleic acid ligands can be conjugated to any other reagent that is capable of binding to a particular analyte. For example, the nucleic acid ligand could be conjugated to antibodies, proteins, sugars or peptides. Such reagents may have longer shelf-lives than traditional antibody-conjugated calf intestinal phosphatase, as the actual enzyme is added separately from the ligand-conjugated detection reagent.

Inhibitory nucleic acid ligands of calf intestinal phosphatase also have great utility. Inhibitory calf intestinal phosphatase nucleic acid ligands could be used in a homogeneous assay system for the detection of proteins. In this embodiment, an inhibitory CIP nucleic acid ligand is synthesized contiguously with a nucleic acid ligand specific for an independent target analyte such that the binding of CIP and the target analyte are mutually exclusive. The system is designed with CIP, CIP substrate and the nucleic acid ligand present at concentrations that nearly completely inhibit CIP activity. Addition of the test solution containing the specific analyte will result in the release of CIP from the nucleic acid ligand. Thus increasing concentrations of analyte will be directly proportional to the CIP signal achieved. Inhibitory nucleic acid ligand can be used without modification, but if necessary stronger CIP inhibitors can be created by conjugating a small molecule CIP inhibitor to the aptamer or by adding a large molecular weight moiety such as polyethylene glycol, dextran, to help the inhibitory properties via steric hindrance. Naturally, any of these embodiments are not limited to CIP as the reporter enzyme, but are equally applicable to other enzyme reporters including, but not limited to, enzymes such as peroxidase, beta-galactosidase, glucose-6-phosphate dehydrogenase, and glucose oxidase.

The SELEX target of the instant invention, CIP, can be immobilized solely through hydrophobic interactions with the surface of a microtiter plate during the SELEX process. This immobilization to a solid support allows the washing and elution steps to be carried out in the microtiter plate. Previous embodiments of the SELEX process have immobilized targets to solid supports by modifying the target in some way. Such modifications require manipulation of the targets and are often time consuming. By contrast, the hydrophobic immobilization method provided by the instant invention is extremely simple, requiring no manipulation of the target. Moreover, the use of a robotics-compatible microtiter plate format allows the SELEX process to be automated.

EXAMPLES

The following examples are given by way of illustration only. They are not to be taken as limiting the scope of the present invention.

Example 1

Use of SELEX to Obtain Nucleic Acid Ligands to Calf Intestinal Phosphatase

Calf intestinal alkaline phosphatase (10 mg/ml; molecular weight 52,486 Daltons) was purchased from Boehringer Mannheim (Indianapolis, Ind.). Single-stranded DNA-primers and templates were synthesized by Operon Technologies Inc. (Alameda, Calif.).

The SELEX-process has been described in detail in: Fitzwater and Polisky (1996) Methods Enzymol. 267:275–301. In brief, double stranded transcription templates were prepared by Klenow fragment extension of 40N8 ssDNA: 5'-gcctgttgtgagcctcctgtcgaa($n_{40}$) ttgagcgtttattcttgtctccc 3'(SEQ ID NO:44) using the 5N8 primer: 5'-taatacgactcactatagggagacaagaataaacgctcaa-3' (SEQ ID NO:45) that contains the T7 polymerase promoter (underlined). RNA was prepared with T7 RNA polymerase as described previously in Fitzwater and Polisky (1996) Methods Enzymol. 267:275–301, incorporated herein by reference in its entirety. All transcription reactions were performed in the presence of pyrimidine nucleotides that were 2'-fluoro (2'-F) modified on the sugar moiety. This substitution confers enhanced resistance to ribonucleases that utilize the 2'-hydroxyl moiety for cleavage of the phosphodiester bond. Specifically, each transcription mixture contained 3.3 mM 2'-F UTP and 3.3 mM 2'-F CTP along with 1 mM GTP and ATP. The initial randomized RNA library thus produced comprised $3 \times 10^{14}$ molecules (535 picomoles).

Eight rounds of SELEX were performed using this randomized RNA library. For each round, Lumino plates (Labsystems, Needham Heights, Mass.) were coated for 2 hours at room temperature with 200 μl Dulbecco's PBS containing CIP concentrations as shown in Table 1. After coating, wells were blocked using Superblock Blocking buffer in TBS (Pierce Chemical company, Rockford, Ill.) for rounds 1 to 3 while for rounds 5 to 8 wells were blocked with SHMCK+buffer [20 mM Hepes, pH 7.35, 120 mM NaCl, 5 mM KCl, 1 mM $CaCl_2$, 1 mM $MgCl_2$ and 1 g/liter casein (I-block; Tropix)]. Binding and wash buffer consisted of SHMCK+buffer containing 0.05% Tween 20. For each SELEX round, RNA was diluted into 200 μl of binding buffer and allowed to incubate for 2 hours at 37° C. in the protein coated wells that were pre-washed with binding buffer. RNA input into each round is shown in Table 1. After binding, six washes of 200 μl each were performed. Following the wash step, the dry well was placed on top of a 95° C. heat block for 5 minutes. Standard AMV reverse transcriptase reactions (50 μl) were performed at 48° C. directly in the well and the reaction products utilized for standard PCR and transcription reactions. Two synthetic primers 5N8 (see above) and 3N8: 5'-gcctgttgtgagcctcctgtcgaa-3' (SEQ ID NO:46) were used for these template amplification and reverse transcription steps. For rounds six through eight, transcriptions were performed in the presence of biotin-GAP in order to biotinylate the 5'-termini of the RNA pool.

The amplified affinity enriched round 8 pool was purified on an 8% polyacrylamide gel, reverse transcribed into ssDNA and the DNA amplified by the polymerase chain reaction (PCR) using primers containing BamHI and HindIII restriction endonuclease sites. PCR fragments were cloned, plasmids prepared and sequence analyses performed according to standard techniques (Sambrook et al. (1989) *Molecular Cloning: A Laboratory Manual*, $2^{nd}$ Ed. 3 vols., Cold Spring Harbor Laboratory Press, Cold Spring Harbor). The sequences of 43 individual clones are shown in FIG. 1. The majority of these clones (39) represent one of two distinct sequences designated group A and group B (FIG. 1). Sequences obtained from twelve clones were members of group A while sequences obtained from 27 clones were members of group B. Examination of the variable region of the 12 clones in group A revealed 9 unique, although highly similar, sequences. Examination of the variable region of the 27 clones in group B revealed only 7 unique sequences and these do not differ by more than a few nucleotides (FIG. 1). In fact, 21 of the sequences are identical and can be represented by clone DD-172-2-20 (SEQ ID No: 13) shown at the top of the group B section of FIG. 1. Finally four individual sequences were obtained and placed arbitrarily into group C (FIG. 1). Overall, this data represents a highly enriched sequence pool.

Example 2
Affinity Determinations of Affinity Enriched Pool of Nucleic Acid Ligands and of Individual Calf Intestinal Phosphatase Nucleic Acid Ligands The affinity of the initial random library and round 8 affinity enriched pool of Example 1 was performed by a plate-based assay using RNA-transcripts biotinylated on the 5'-terminus. Briefly, opaque white 96-well Lumino plates were coated with streptavidin (10 to 20 μg/well). Biotinylated RNA obtained either from the round 8 pool or the random library were added separately to individual wells of a 96-well microtiter plate (approximately 30 fMols RNA per well). After incubating for 1 hour at room temperature, wells were washed three times with 200 ml of SHMCK+buffer. Varying concentrations of CIP, in SHMCK+buffer, were added to the wells and allowed to incubate for 1 hour at 37° C. Wells were washed four times with 200 μl SHMCK+buffer followed by the addition of a 100 μl solution consisting of 0.1 M diethanolamine pH 10, 10% volume/volume Sapphire enhancer solution (Tropix Inc., Bedford, Mass.), 17 ml/ml CSPD (Tropix, Inc.), 1 mM $MgCl_2$, and 0.02% sodium azide. After a 30 minute incubation, chemiluminescence was measured using a Berthold (Nashua, N.H.) LB 96P luminometer. Luminescence levels were integrated over one second and data were fit to a sigmoidal dose-response curve (variable slope), Y=Bottom+[(Top−Bottom)/1+10$^{(Log\ EC50-x)(Hillslope)}$] using GraphPad Prism version 2.01 (GraphPad Software; San Diego, Calif.). Each replicate was considered individually and convergence was obtained when two consecutive iterations varied the sum of squares (relative distance of the points from the curve, $1/Y^2$) by less than 0.01%.

Figure 3:
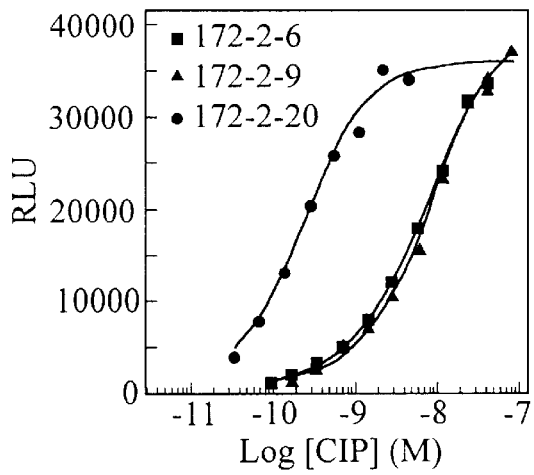
FIG. 3 depicts CIP binding isotherms for the determination of the equilibrium dissociation constant at 37° C. for individual clones from the round 8 SELEX pool. Data are shown as the mean +/–the SEM for duplicate determinations at each point.

Using this procedure, the affinity-enriched round 8 pool had an equilibrium dissociation constant (Kd) for CIP at 37° C. of $250 \times 10^{-12}$ M (FIG. 2; RLU is relative luminescence units). Two representatives of group B, DD-172-2-20 and DD-172-2-4, were tested and displayed subnanomolar dissociation constants (260 pM and 130 pM respectively). Individual members of group A (DD-172-2-9, DD-172-2-17) and the one member of group C (DD-172-2-6) were also tested and displayed low nanomolar dissociation constants. (Table 2 and FIG. 3).

Example 3
Measurement of Inhibitory Activity of Calf Intestinal Phosphatase Nucleic Acid Ligands CIP was diluted into SHMCK+buffer (without detergent) to a concentration of 1 nM. This solution was divided into 250 μl aliquots and a separate nucleic acid ligand from Example 2 or random RNA-library added to an individual aliquot such that the final aptamer concentration was 100 nM. The volumes of nucleic acid ligand addition ranged from 1.3 to 3.6 μl and thus did not significantly alter the concentration of CIP. As a control, one aliquot received 2.5 μl of water. Solutions were allowed to incubate for 10 minutes at room temperature followed by the transfer of two 100 μl aliquots, from each original 250 μl aliquot, to duplicate wells of a microtiter plate. After an additional five minute incubation, 100 μl of 43.6 mM p-Nitrophenyl Phosphate chromagenic substrate (pNPP; Sigma, Saint Louis, Mo.) in SHMCK buffer (no detergent and no protein) was added. After 45 minutes the absorbance at 405 nm was determined using a microplate reader. Final absorbance values were calculated by subtracting the background absorbance as determined from duplicate wells containing 200 μl of the identical solution except without the presence of CIP.

Figure 4:
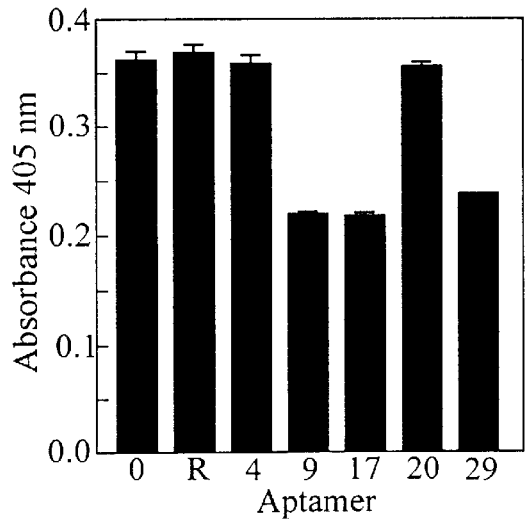
FIG. 4 depicts CIP inhibition experiments. Random 2'-F RNA (R), along with the nucleic acid ligand sequences DD-172-2-4 (4) (SEQ ID NO:35), DD-172-2-9 (9) (SEQ ID NO:8), DD-172-2-17 (17) (SEQ ID NO:2), DD-172-2-20 (20) (SEQ ID NO:13) and DD 29 (29) (SEQ ID NO:3), were tested for their ability to inhibit the activity of CIP. Data are shown as the mean +/–the standard deviation for duplicate determinations. Data from each group were compared to CIP activity in the absence of added nucleic acid (0).

As shown in FIG. 4, under the conditions of this assay neither a 2'-F pyrimidine random RNA-library (R) or group 2 clones DD-172-2-4 (4) and DD-172-2-20 (20) were able to inhibit the activity of CIP. However, clones obtained from group 1, namely DD-172-2-9 (9), DD-172-2-17 (17) and DD-172-2-29 (29), reduced the observed CIP activity by 40% despite the fact that the substrate concentration (21.8 mM) was over 400,000 times greater than the aptamer consentration (50 nM). Of course the Km of CIP for pNPP has not been determined for the buffer conditions utilized here.

TABLE 1

SELEX RNA and protein input.

| Round | CIP (pMol/well) | RNA (pMol/well) |
|---|---|---|
| 1 | 95 | 535 |
| 2 | 38 | 240 |
| 3 | 38 | 80 |
| 4 | 38 | 60 |
| 5 | 38 | 50 |

TABLE 1-continued

SELEX RNA and protein input.

| Round | CIP (pMol/well) | RNA (pMol/well) |
|---|---|---|
| 6 | 38 | 50 |
| 7 | 38 | 43 |
| 8 | 3.8 | 20 |

TABLE 2

Equilibrium dissociation constants for individual 2'-F pyrimidine RNA-aptamers at 37° C.

| Clone | Kd (pM) |
|---|---|
| 172-2-4 | 130 |
| 172-2-20 | 260 |
| 172-2-17 | 7200 |
| 172-2-9 | 7800 |
| 172-2-6 | 7900 |

What is claimed is:

1. A method of identifying nucleic acid ligands to calf intestinal phosphatase (CIP), the method comprising:
   a) preparing a candidate mixture of nucleic acids;
   b) contacting the candidate mixture of nucleic acids with CIP, wherein nucleic acids having an increased affinity to CIP relative to the candidate mixture may be partitioned from the remainder of the candidate mixture;
   c) partitioning the increased affinity nucleic acids from the remainder of the candidate mixture; and
   d) amplifying the increased affinity nucleic acids to yield a mixture of nucleic acids enriched for nucleic acids with relatively higher affinity and specificity for binding to CIP, whereby a nucleic acid ligand of CIP may be identified.

2. The method of claim 1 further comprising:
   e) repeating steps b), c), and d).

3. The method of claim 1 wherein said candidate mixture of nucleic acids is comprised of single stranded nucleic acids.

4. The method of claim 3 wherein said single stranded nucleic acids are ribonucleic acids.

5. The method of claim 3 wherein said single stranded nucleic acids are deoxyribonucleic acids.

6. The method of claim 4 wherein said nucleic acids are 2'-F (2'-fluoro) modified ribonucleic acids.

* * * * *

SEQUENCE LISTING

```
<160> NUMBER OF SEQ ID NOS: 46

<210> SEQ ID NO 1
<211> LENGTH: 87
<212> TYPE: RNA
<213> ORGANISM: Artificial Sequence
<220> FEATURE:
<221> NAME/KEY: modified_base
<222> LOCATION: (1)..(87)
<223> OTHER INFORMATION: All pyrimidines are 2'F.
<223> OTHER INFORMATION: Description of Artificial  Sequence:  Synthetic
      Sequence

<400> SEQUENCE: 1
gggagacaag aauaaacgcu caaacauaaa acaaaauaac cuuagccucg g ugcucuacg      60 caauucgaca ggaggcucac aucaggc                                          87

<210> SEQ ID NO 2
<211> LENGTH: 85
<212> TYPE: RNA
<213> ORGANISM: Artificial Sequence
<220> FEATURE:
<221> NAME/KEY: modified_base
<222> LOCATION: (1)..(85)
<223> OTHER INFORMATION: All pyrimidines are 2'F.
<223> OTHER INFORMATION: Description of Artificial  Sequence:  Synthetic
      Sequence

<400> SEQUENCE: 2
gggagacaag aauaacgcuc aaacacaaaa caaaauaacu uggccucggu g cucuacgca      60 auucgacagg aggcucacaa caggc                                            85

<210> SEQ ID NO 3
<211> LENGTH: 88
```

```
<212> TYPE: RNA
<213> ORGANISM: Artificial Sequence
<220> FEATURE:
<221> NAME/KEY: modified_base
<222> LOCATION: (1)..(88)
<223> OTHER INFORMATION: All pyrimidines are 2'F.
<223> OTHER INFORMATION: Description of Artificial  Sequence: Synthetic
      Sequence

<400> SEQUENCE: 3
gggagacaag aauaaacgcu caaacacaaa acaaaaauaa ccuuagccuc g gugcucuac     60 gcaauucgac aggaggcuca caacaggc                                         88

<210> SEQ ID NO 4
<211> LENGTH: 86
<212> TYPE: RNA
<213> ORGANISM: Artificial Sequence
<220> FEATURE:
<221> NAME/KEY: modified_base
<222> LOCATION: (1)..(86)
<223> OTHER INFORMATION: All pyrimidines are 2'F.
<223> OTHER INFORMATION: Description of Artificial  Sequence: Synthetic
      Sequence

<400> SEQUENCE: 4
gggagacaag aaaaacgcuc aaacacaaaa caaaauaacc uuagccucgg u gcucuacgc     60 aauucgacag gaggcucaca acaggc                                           86

<210> SEQ ID NO 5
<211> LENGTH: 88
<212> TYPE: RNA
<213> ORGANISM: Artificial Sequence
<220> FEATURE:
<221> NAME/KEY: modified_base
<222> LOCATION: (1)..(88)
<223> OTHER INFORMATION: All pyrimidines are 2'F.
<223> OTHER INFORMATION: Description of Artificial  Sequence: Synthetic
      Sequence

<400> SEQUENCE: 5
gggagacaag aauaaacgcu caaacacaaa acaaaauaac cuuagccucg g ugcucuacg     60 caauucgaca ggaggcucac aacaggcg                                         88

<210> SEQ ID NO 6
<211> LENGTH: 87
<212> TYPE: RNA
<213> ORGANISM: Artificial Sequence
<220> FEATURE:
<221> NAME/KEY: modified_base
<222> LOCATION: (1)..(87)
<223> OTHER INFORMATION: All pyrimidines are 2'F.
<223> OTHER INFORMATION: Description of Artificial  Sequence: Synthetic
      Sequence

<400> SEQUENCE: 6
gggagacaag aauaaacgcu caaacacaaa acaagauaac cuuagccucg g ugcucuacg     60 caauucgaca ggaggcucac aacaggc                                          87

<210> SEQ ID NO 7
<211> LENGTH: 86
<212> TYPE: RNA
<213> ORGANISM: Artificial Sequence
<220> FEATURE:
<221> NAME/KEY: modified_base
<222> LOCATION: (1)..(86)
<223> OTHER INFORMATION: All pyrimidines are 2'F.
<223> OTHER INFORMATION: Description of Artificial  Sequence: Synthetic
```

Sequence

<400> SEQUENCE: 7
gggagacaag aauaaacgcu caaacacaaa acaaaaaacc uuagccucgg u gcucuacgc      60 aauucgacag gaggaucaca acaggc      86

<210> SEQ ID NO 8
<211> LENGTH: 86
<212> TYPE: RNA
<213> ORGANISM: Artificial Sequence
<220> FEATURE:
<221> NAME/KEY: modified_base
<222> LOCATION: (1)..(86)
<223> OTHER INFORMATION: All pyrimidines are 2'F.
<223> OTHER INFORMATION: Description of Artificial  Sequence: Synthetic
      Sequence

<400> SEQUENCE: 8
gggagacaag aauaaacgcu caacacaaaa caaaauaacc uuagccucgg u gcucuacgc      60 aaucgacag gaggcucaca acaggc      86

<210> SEQ ID NO 9
<211> LENGTH: 86
<212> TYPE: RNA
<213> ORGANISM: Artificial Sequence
<220> FEATURE:
<221> NAME/KEY: modified_base
<222> LOCATION: (1)..(86)
<223> OTHER INFORMATION: All pyrimidines are 2'F.
<223> OTHER INFORMATION: Description of Artificial  Sequence: Synthetic
      Sequence

<400> SEQUENCE: 9
gggagacaag aauaaacgcu caacacaaaa caaaauaacc uuagccucgg u gcucuacgc      60 aaucgacag gaggcucaca acaggc      86

<210> SEQ ID NO 10
<211> LENGTH: 86
<212> TYPE: RNA
<213> ORGANISM: Artificial Sequence
<220> FEATURE:
<221> NAME/KEY: modified_base
<222> LOCATION: (1)..(86)
<223> OTHER INFORMATION: All pyrimidines are 2'F.
<223> OTHER INFORMATION: Description of Artificial  Sequence: Synthetic
      Sequence

<400> SEQUENCE: 10
gggagacaag aauaaacgcu caacacaaaa caaaauaacc uuagccucgg u gcucuacgc      60 aaucgacag aaggcucaca acaggc      86

<210> SEQ ID NO 11
<211> LENGTH: 85
<212> TYPE: RNA
<213> ORGANISM: Artificial Sequence
<220> FEATURE:
<221> NAME/KEY: modified_base
<222> LOCATION: (1)..(85)
<223> OTHER INFORMATION: All pyrimidines are 2'F.
<223> OTHER INFORMATION: Description of Artificial  Sequence: Synthetic
      Sequence

<400> SEQUENCE: 11
gggagacaag aauaaacgcu caaacaaaac aaaauaaccc uagccucggu g cucuacgca      60 auucgacagg aggcucacaa caggc      85

<210> SEQ ID NO 12
<211> LENGTH: 86
<212> TYPE: RNA
<213> ORGANISM: Artificial Sequence
<220> FEATURE:
<221> NAME/KEY: modified_base
<222> LOCATION: (1)..(86)
<223> OTHER INFORMATION: All pyrimidines are 2'F.
<223> OTHER INFORMATION: Description of Artificial Sequence: Synthetic
      Sequence

<400> SEQUENCE: 12
gggagacaag aauaaacgcu caaacaaaaa caaaaaauac uuagccucgg u gcucuacgc      60 aauucgacag gaggcucaca acaggc                                            86

<210> SEQ ID NO 13
<211> LENGTH: 86
<212> TYPE: RNA
<213> ORGANISM: Artificial Sequence
<220> FEATURE:
<221> NAME/KEY: modified_base
<222> LOCATION: (1)..(86)
<223> OTHER INFORMATION: All pyrimidines are 2'F.
<223> OTHER INFORMATION: Description of Artificial Sequence: Synthetic
      Sequence

<400> SEQUENCE: 13
gggagacaag aauaaacgcu caacgccagg cccuuaucaa gcgcggaacg c augacccgu      60 cuuucgacag gaggcucaca acaggc                                            86

<210> SEQ ID NO 14
<211> LENGTH: 86
<212> TYPE: RNA
<213> ORGANISM: Artificial Sequence
<220> FEATURE:
<221> NAME/KEY: modified_base
<222> LOCATION: (1)..(86)
<223> OTHER INFORMATION: All pyrimidines are 2'F.
<223> OTHER INFORMATION: Description of Artificial Sequence: Synthetic
      Sequence

<400> SEQUENCE: 14
gggagacaag aauaaacgcu caacgccagg cccuuaucaa gcgcggaacg c augacccgu      60 cuuucgacag gaggcucaca acaggc                                            86

<210> SEQ ID NO 15
<211> LENGTH: 86
<212> TYPE: RNA
<213> ORGANISM: Artificial Sequence
<220> FEATURE:
<221> NAME/KEY: modified_base
<222> LOCATION: (1)..(86)
<223> OTHER INFORMATION: All pyrimidines are 2'F.
<223> OTHER INFORMATION: Description of Artificial Sequence: Synthetic
      Sequence

<400> SEQUENCE: 15
gggagacaag aauaaacgcu caacgccagg cccuuaucaa gcgcggaacg c augacccgu      60 cuuucgacag gaggcucaca acaggc                                            86

<210> SEQ ID NO 16
<211> LENGTH: 86
<212> TYPE: RNA
<213> ORGANISM: Artificial Sequence
<220> FEATURE:

<221> NAME/KEY: modified_base
<222> LOCATION: (1)..(86)
<223> OTHER INFORMATION: All pyrimidines are 2'F.
<223> OTHER INFORMATION: Description of Artificial  Sequence: Synthetic
      Sequence

<400> SEQUENCE: 16
gggagacaag aauaaacgcu caacgccagg cccuuaucaa gcgcggaacg c augacccgu    60 cuuucgacug gaggcucaca acaggc                                          86

<210> SEQ ID NO 17
<211> LENGTH: 86
<212> TYPE: RNA
<213> ORGANISM: Artificial Sequence
<220> FEATURE:
<221> NAME/KEY: modified_base
<222> LOCATION: (1)..(86)
<223> OTHER INFORMATION: All pyrimidines are 2'F.
<223> OTHER INFORMATION: Description of Artificial  Sequence: Synthetic
      Sequence

<400> SEQUENCE: 17
nggagacaag aauaaacgcu caacgccagg cccuuaucaa gcgcggaacg c augacccgu    60 cuuucgacag gaggcucaca acaggc                                          86

<210> SEQ ID NO 18
<211> LENGTH: 86
<212> TYPE: RNA
<213> ORGANISM: Artificial Sequence
<220> FEATURE:
<221> NAME/KEY: modified_base
<222> LOCATION: (1)..(86)
<223> OTHER INFORMATION: All pyrimidines are 2'F.
<223> OTHER INFORMATION: Description of Artificial  Sequence: Synthetic
      Sequence

<400> SEQUENCE: 18
gggagacaag aauaaacgcu caacgccagg cccuuaucaa gcgcggaacg c augacccgu    60 cuuucgacag gaggcucaca acaggc                                          86

<210> SEQ ID NO 19
<211> LENGTH: 86
<212> TYPE: RNA
<213> ORGANISM: Artificial Sequence
<220> FEATURE:
<221> NAME/KEY: modified_base
<222> LOCATION: (1)..(86)
<223> OTHER INFORMATION: All pyrimidines are 2'F.
<223> OTHER INFORMATION: Description of Artificial  Sequence: Synthetic
      Sequence

<400> SEQUENCE: 19
gggagacaag aauaaacgcu caacgccagg cccuuaucaa gcgcggaacg c augacccgu    60 cuuucgacag gaggcucaca acaggc                                          86

<210> SEQ ID NO 20
<211> LENGTH: 86
<212> TYPE: RNA
<213> ORGANISM: Artificial Sequence
<220> FEATURE:
<221> NAME/KEY: modified_base
<222> LOCATION: (1)..(86)
<223> OTHER INFORMATION: All pyrimidines are 2'F.
<223> OTHER INFORMATION: Description of Artificial  Sequence: Synthetic
      Sequence

<400> SEQUENCE: 20
gggagacaag aauaaacgcu caacgccagg cccuuaucaa gcgcggaacg c augacccgu        60 cuuucgacag gaggcucaca ucaggc                                              86

<210> SEQ ID NO 21
<211> LENGTH: 86
<212> TYPE: RNA
<213> ORGANISM: Artificial Sequence
<220> FEATURE:
<221> NAME/KEY: modified_base
<222> LOCATION: (1)..(86)
<223> OTHER INFORMATION: All pyrimidines are 2'F.
<223> OTHER INFORMATION: Description of Artificial  Sequence:  Synthetic
      Sequence

<400> SEQUENCE: 21
gggagacaag aauaaacgcu caacgccagg cccuuaucaa gcgcggaacg c augacccgu        60 cuuucgacag gaggcucaca acaggc                                              86

<210> SEQ ID NO 22
<211> LENGTH: 84
<212> TYPE: RNA
<213> ORGANISM: Artificial Sequence
<220> FEATURE:
<221> NAME/KEY: modified_base
<222> LOCATION: (1)..(84)
<223> OTHER INFORMATION: All pyrimidines are 2'F.
<223> OTHER INFORMATION: Description of Artificial  Sequence:  Synthetic
      Sequence

<400> SEQUENCE: 22
gagacaagaa uaaacgcuca acgccaggcc cuuaucaagc gcggaacgca u gacccgucu        60 uucgacagga ggcucacaac aggc                                                84

<210> SEQ ID NO 23
<211> LENGTH: 85
<212> TYPE: RNA
<213> ORGANISM: Artificial Sequence
<220> FEATURE:
<221> NAME/KEY: modified_base
<222> LOCATION: (1)..(85)
<223> OTHER INFORMATION: All pyrimidines are 2'F.
<223> OTHER INFORMATION: Description of Artificial  Sequence:  Synthetic
      Sequence

<400> SEQUENCE: 23
gggagacaag aauaaacgcu caacgccagg cccuuaucaa gcgcggaacg c augacccgu        60 cuuucgacag gaggcucaca acagc                                               85

<210> SEQ ID NO 24
<211> LENGTH: 85
<212> TYPE: RNA
<213> ORGANISM: Artificial Sequence
<220> FEATURE:
<221> NAME/KEY: modified_base
<222> LOCATION: (1)..(85)
<223> OTHER INFORMATION: All pyrimidines are 2'F.
<223> OTHER INFORMATION: Description of Artificial  Sequence:  Synthetic
      Sequence

<400> SEQUENCE: 24
gggagacaag auaaacgcuc aacgccaggc ccuuaucaag cgcggaacgc a ugacccguc        60 uuucgacagg aggcucacaa caggc                                               85

<210> SEQ ID NO 25

<211> LENGTH: 88
<212> TYPE: RNA
<213> ORGANISM: Artificial Sequence
<220> FEATURE:
<221> NAME/KEY: modified_base
<222> LOCATION: (1)..(88)
<223> OTHER INFORMATION: All pyrimidines are 2'F.
<223> OTHER INFORMATION: Description of Artificial Sequence: Synthetic
      Sequence

<400> SEQUENCE: 25
gggagacaag aauaaacgcu caacgccagg cccuuaucaa gcgcggaacg c augacccgu      60 cuuucgacag gaggggcuca caacaggc                                          88

<210> SEQ ID NO 26
<211> LENGTH: 86
<212> TYPE: RNA
<213> ORGANISM: Artificial Sequence
<220> FEATURE:
<221> NAME/KEY: modified_base
<222> LOCATION: (1)..(86)
<223> OTHER INFORMATION: All pyrimidines are 2'F.
<223> OTHER INFORMATION: Description of Artificial Sequence: Synthetic
      Sequence

<400> SEQUENCE: 26
gggagacaag auuaaacgcu caacgccagg cccuuaucaa gcgcggaacg c augacccgu      60 cuuucgacag gaggcucaca acaggc                                            86

<210> SEQ ID NO 27
<211> LENGTH: 86
<212> TYPE: RNA
<213> ORGANISM: Artificial Sequence
<220> FEATURE:
<221> NAME/KEY: modified_base
<222> LOCATION: (1)..(86)
<223> OTHER INFORMATION: All pyrimidines are 2'F.
<223> OTHER INFORMATION: Description of Artificial Sequence: Synthetic
      Sequence

<400> SEQUENCE: 27
gggagacaag aaucaacgcu caacgccagg cccuuaucaa gcgcggaacg c augacccgu      60 cuuucgacag gaggcucaca acaggc                                            86

<210> SEQ ID NO 28
<211> LENGTH: 86
<212> TYPE: RNA
<213> ORGANISM: Artificial Sequence
<220> FEATURE:
<221> NAME/KEY: modified_base
<222> LOCATION: (1)..(86)
<223> OTHER INFORMATION: All pyrimidines are 2'F.
<223> OTHER INFORMATION: Description of Artificial Sequence: Synthetic
      Sequence

<400> SEQUENCE: 28
gggagacaag aauaaacgcu caacgccagg cccuuaucaa gcgcggaacg c augacccgu      60 cuuucgacag gaggcucaca acaggc                                            86

<210> SEQ ID NO 29
<211> LENGTH: 86
<212> TYPE: RNA
<213> ORGANISM: Artificial Sequence
<220> FEATURE:
<221> NAME/KEY: modified_base
<222> LOCATION: (1)..(86)
<223> OTHER INFORMATION: All pyrimidines are 2'F.

<223> OTHER INFORMATION: Description of Artificial Sequence: Synthetic
      Sequence

<400> SEQUENCE: 29
gggagacaag aauaaacgcu caacgccagg cccuuaucaa gcgcggaacg c augacccgu      60 cuuucgacag gaggcucaca acaggc      86

<210> SEQ ID NO 30
<211> LENGTH: 86
<212> TYPE: RNA
<213> ORGANISM: Artificial Sequence
<220> FEATURE:
<221> NAME/KEY: modified_base
<222> LOCATION: (1)..(86)
<223> OTHER INFORMATION: All pyrimidines are 2'F.
<223> OTHER INFORMATION: Description of Artificial Sequence: Synthetic
      Sequence

<400> SEQUENCE: 30
gggagacaag aauaaacgcu caacgccagg cccuuaucaa gcgcggaacg c augacccgu      60 cuuucgacag gaggcucaca acaggc      86

<210> SEQ ID NO 31
<211> LENGTH: 86
<212> TYPE: RNA
<213> ORGANISM: Artificial Sequence
<220> FEATURE:
<221> NAME/KEY: modified_base
<222> LOCATION: (1)..(86)
<223> OTHER INFORMATION: All pyrimidines are 2'F.
<223> OTHER INFORMATION: Description of Artificial Sequence: Synthetic
      Sequence

<400> SEQUENCE: 31
gggagacaag aauaaacgcu caacgccagg cccuuaucaa gcgcggaacg c augacccgu      60 cuuucgacag gaggcucaca acaggc      86

<210> SEQ ID NO 32
<211> LENGTH: 86
<212> TYPE: RNA
<213> ORGANISM: Artificial Sequence
<220> FEATURE:
<221> NAME/KEY: modified_base
<222> LOCATION: (1)..(86)
<223> OTHER INFORMATION: All pyrimidines are 2'F.
<223> OTHER INFORMATION: Description of Artificial Sequence: Synthetic
      Sequence

<400> SEQUENCE: 32
gggagacaag aauaaacgcu caacgccagg cccuuaucaa gcgcggaacg c augacccgu      60 cuuucgacag gaggcucaca acaggc      86

<210> SEQ ID NO 33
<211> LENGTH: 85
<212> TYPE: RNA
<213> ORGANISM: Artificial Sequence
<220> FEATURE:
<221> NAME/KEY: modified_base
<222> LOCATION: (1)..(85)
<223> OTHER INFORMATION: All pyrimidines are 2'F.
<223> OTHER INFORMATION: Description of Artificial Sequence: Synthetic
      Sequence

<400> SEQUENCE: 33
gggagacaag aauaaacgcu caacgccagg cccuuaucaa gcgcggaacg c augacccgu      60

<210> SEQ ID NO 34
<211> LENGTH: 85
<212> TYPE: RNA
<213> ORGANISM: Artificial Sequence
<220> FEATURE:
<221> NAME/KEY: modified_base
<222> LOCATION: (1)..(85)
<223> OTHER INFORMATION: All pyrimidines are 2'F.
<223> OTHER INFORMATION: Description of Artificial Sequence: Synthetic Sequence

<400> SEQUENCE: 34
gggagacaag aauaaacgcu caacgccagg ccccuaucaa gcgcggaacg c augacccgu      60 cuuucgacag gaggcucaca acagc                                            85

<210> SEQ ID NO 35
<211> LENGTH: 86
<212> TYPE: RNA
<213> ORGANISM: Artificial Sequence
<220> FEATURE:
<221> NAME/KEY: modified_base
<222> LOCATION: (1)..(86)
<223> OTHER INFORMATION: All pyrimidines are 2'F.
<223> OTHER INFORMATION: Description of Artificial Sequence: Synthetic Sequence

<400> SEQUENCE: 35
gggagacaag aauaaacgcu caacgccagg cccuuaucaa gcgcggaacg c acgacccgu      60 cuuucgacag gaggcucaca acaggc                                           86

<210> SEQ ID NO 36
<211> LENGTH: 86
<212> TYPE: RNA
<213> ORGANISM: Artificial Sequence
<220> FEATURE:
<221> NAME/KEY: modified_base
<222> LOCATION: (1)..(86)
<223> OTHER INFORMATION: All pyrimidines are 2'F.
<223> OTHER INFORMATION: Description of Artificial Sequence: Synthetic Sequence

<400> SEQUENCE: 36
gggagacaag aauaaacgcu caacgccagg cccuuaucaa gcguggaacg c augacccgu      60 cuuucgacag gaggcucaca acaggc                                           86

<210> SEQ ID NO 37
<211> LENGTH: 86
<212> TYPE: RNA
<213> ORGANISM: Artificial Sequence
<220> FEATURE:
<221> NAME/KEY: modified_base
<222> LOCATION: (1)..(86)
<223> OTHER INFORMATION: All pyrimidines are 2'F.
<223> OTHER INFORMATION: Description of Artificial Sequence: Synthetic Sequence

<400> SEQUENCE: 37
gggagacaag aauaaacgcu caacgccagg cccuuaucaa gcgcggaacg c augacccgu     60 cauucgacag gaggcucaca acaggc                                           86

<210> SEQ ID NO 38
<211> LENGTH: 86
<212> TYPE: RNA
<213> ORGANISM: Artificial Sequence

```
<220> FEATURE:
<221> NAME/KEY: modified_base
<222> LOCATION: (1)..(86)
<223> OTHER INFORMATION: All pyrimidines are 2'F.
<223> OTHER INFORMATION: Description of Artificial  Sequence: Synthetic
      Sequence

<400> SEQUENCE: 38
gggagacaag aauaaacgcu caaugccagg cccuuaucaa gcgcggaacg c augacccgu        60 cuuucgacag gaggcucaca acaggc                                             86

<210> SEQ ID NO 39
<211> LENGTH: 85
<212> TYPE: RNA
<213> ORGANISM: Artificial Sequence
<220> FEATURE:
<221> NAME/KEY: modified_base
<222> LOCATION: (1)..(85)
<223> OTHER INFORMATION: All pyrimidines are 2'F.
<223> OTHER INFORMATION: Description of Artificial  Sequence: Synthetic
      Sequence

<400> SEQUENCE: 39
gggagacaag aauaaacgcu caagccaggc ccuuaucaag cgcggaacgc a ugacccguc        60 uuucgacagg aggcucacaa caggc                                              85

<210> SEQ ID NO 40
<211> LENGTH: 87
<212> TYPE: RNA
<213> ORGANISM: Artificial Sequence
<220> FEATURE:
<221> NAME/KEY: modified_base
<222> LOCATION: (1)..(87)
<223> OTHER INFORMATION: All pyrimidines are 2'F.
<223> OTHER INFORMATION: Description of Artificial  Sequence: Synthetic
      Sequence

<400> SEQUENCE: 40
gggagacaag aauaaacgcu caaguaaaag ccucauagaa cuaacuaaca a cgcgcucac        60 ggauucgaca ggaggcucac aacaggc                                            87

<210> SEQ ID NO 41
<211> LENGTH: 85
<212> TYPE: RNA
<213> ORGANISM: Artificial Sequence
<220> FEATURE:
<221> NAME/KEY: modified_base
<222> LOCATION: (1)..(85)
<223> OTHER INFORMATION: All pyrimidines are 2'F.
<223> OTHER INFORMATION: Description of Artificial  Sequence: Synthetic
      Sequence

<400> SEQUENCE: 41
gggagacaag aauaaacgcu caacgucaua aauguaaaca ggauuauaag c gcgaccuag        60 auucgacagg aggcucacaa caggc                                              85

<210> SEQ ID NO 42
<211> LENGTH: 81
<212> TYPE: RNA
<213> ORGANISM: Artificial Sequence
<220> FEATURE:
<221> NAME/KEY: modified_base
<222> LOCATION: (1)..(81)
<223> OTHER INFORMATION: All pyrimidines are 2'F.
<223> OTHER INFORMATION: Description of Artificial  Sequence: Synthetic
      Sequence
```

```
<400> SEQUENCE: 42
gggagacaag aauaaacgcu caagcgcaaa gccuuucaag cucgugcuau c acugaauuc        60 gacaggaggc ucacaacagg c                                                  81

<210> SEQ ID NO 43
<211> LENGTH: 87
<212> TYPE: RNA
<213> ORGANISM: Artificial Sequence
<220> FEATURE:
<221> NAME/KEY: modified_base
<222> LOCATION: (1)..(87)
<223> OTHER INFORMATION: All pyrimidines are 2'F.
<223> OTHER INFORMATION: Description of Artificial  Sequence: Synthetic
      Sequence

<400> SEQUENCE: 43
gggagacaag aauaaacgcu caacgucccc ccgucaagau cuccucccuc c gcguccccu        60 cccuucgaca ggaggcucac aacaggc                                            87

<210> SEQ ID NO 44
<211> LENGTH: 87
<212> TYPE: DNA
<213> ORGANISM: Artificial Sequence
<220> FEATURE:
<223> OTHER INFORMATION: Description of Artificial  Sequence: Synthetic
      Sequence

<400> SEQUENCE: 44
gcctgttgtg agcctcctgt cgaannnnnn nnnnnnnnnn nnnnnnnnnn n nnnnnnnnn        60 nnnnttgagc gtttattctt gtctccc                                            87

<210> SEQ ID NO 45
<211> LENGTH: 40
<212> TYPE: DNA
<213> ORGANISM: Artificial Sequence
<220> FEATURE:
<223> OTHER INFORMATION: Description of Artificial  Sequence: Synthetic
      Sequence

<400> SEQUENCE: 45
taatacgact cactataggg agacaagaat aaacgctcaa                              40

<210> SEQ ID NO 46
<211> LENGTH: 24
<212> TYPE: DNA
<213> ORGANISM: Artificial Sequence
<220> FEATURE:
<223> OTHER INFORMATION: Description of Artificial  Sequence: Synthetic
      Sequence

<400> SEQUENCE: 46
gcctgttgtg agcctcctgt cgaa                                               24
```